United States Patent [19]

Luft et al.

[11] Patent Number: 5,624,538
[45] Date of Patent: Apr. 29, 1997

[54] MEASURING DEVICE FOR DETERMINING THE CONCENTRATION OF ALCOHOLS

[75] Inventors: Guenter Luft, Lauf; Gerhard Starbeck, Nuernberg, both of Germany

[73] Assignee: Siemens Aktiengesellschaft, München, Germany

[21] Appl. No.: 446,272

[22] Filed: May 22, 1995

[30] Foreign Application Priority Data

May 24, 1994 [DE] Germany ............... 44 18 035.7

[51] Int. Cl.$^6$ .................................................. G01N 27/26
[52] U.S. Cl. ............... 204/418; 204/431; 204/432; 204/415; 422/83; 422/84; 422/88; 422/98
[58] Field of Search ................. 204/400, 415, 204/418, 153.2, 431, 432; 422/83, 84, 88, 98; 205/787

[56] References Cited

U.S. PATENT DOCUMENTS

| | | | |
|---|---|---|---|
| 3,966,579 | 6/1976 | Chang et al. | 204/418 |
| 4,707,336 | 11/1987 | Jones | 422/84 |
| 5,409,785 | 4/1995 | Nakano et al. | 429/33 |

OTHER PUBLICATIONS

Ciprios, G., "Session on Fuel Cell Battery Systems Methanol Fuel Cell Battery," *Annual Proceedings Power Sources Conference*, May 24–26, 1966.

Ang, P. et al., "A Simple Miniaturized Methanol–feed Control for Fuel Cells", *Energy Conversion*, vol. 12 (1972), pp. 65–68. no month available.

*Primary Examiner*—Bruce F. Bell

[57] ABSTRACT

A measuring device for determining the concentration of low-molecular alcohols in water or acid having the following construction:

- a porous anode for the electrochemical oxidation of alcohol
- a cathode for the electrochemical reduction of oxygen
- an ion-conducting membrane arranged between the anode and cathode
- a diffusion-limiting membrane arranged on the side of the anode facing away from the ion-conducting membrane.

18 Claims, No Drawings

MEASURING DEVICE FOR DETERMINING THE CONCENTRATION OF ALCOHOLS

BACKGROUND OF THE INVENTION

1. Field of the Invention

The invention relates to a measuring device for determining the concentration of low-molecular alcohols in water or acids.

2. Description of Related Art

Methanol, a low-molecular alcohol, represents an attractive fuel for electrochemically producing energy in fuel cells. An alkaline liquid electrolyte in particular a potassium hydroxide solution, can be used in fuel cells operated with methanol. However, due to the formation of carbon dioxide during the oxidation of methanol, fuel cells with an acidic electrolyte, such as sulfuric acid, are preferred. Such an electrolyte is very aggressive, especially at elevated temperatures, so that only relatively expensive materials can be used to construct batteries of this type.

For some time, so-called PEM fuel cells have been developed, i.e., fuel cells having a polymer electrolyte membrane (PEM). This cell type is also suited for constructing fuel cells used for the direct conversion of methanol, so-called direct-methanol fuel cells. In this case, the methanol fuel no longer has to be present in an aggressive electrolyte, such as sulfuric acid, rather aqueous methanol solutions can also be used.

In PEM fuel cells operated with methanol—due to the loss of methanol by diffusion through the polymer electrolyte membrane—the methanol concentration at the anode must be adapted as best possible to the existing electrical power level of the fuel battery. For this purpose, a concentration-measuring cell is needed, i.e., a measuring device for determining the concentration of the methanol, which serves as a controlling and monitoring unit in the fuel circuit.

Customary measuring methods for determining the concentration of alcohols are relatively inaccurate or very expensive in the concentration range of 0 to 2 mole/l—due to the only slightly changing physical properties. Electrochemical measuring cells for determining the concentration of alcohols presuppose acidic or alkaline electrolytes, which is likewise disadvantageous (see G. Ciprios, "Proceedings of the 20th Annual Power Sources Conference", May 24–26, 1966; "Energy Conversion", vol. 12 (1972), pp. 65–68).

SUMMARY OF THE INVENTION

The object of the invention is to specify a measuring device which will make it possible to determine the concentration of low-molecular alcohols in aqueous solutions.

This is achieved in accordance with the invention by a measuring device which is characterized by the following features:

- a porous anode for the electrochemical oxidation of alcohol
- a cathode for the electrochemical reduction of oxygen
- an ion-conducting membrane arranged between the anode and cathode
- a diffusion-limiting membrane arranged on the side of the anode facing away from the ion-conducting membrane.

DETAILED DESCRIPTION OF THE INVENTION

The measuring device according to the invention can be operated both in water as well as in acidic liquid electrolytes. The measuring device represents a quasi "direct-alcohol fuel cell" comprising a polymer electrolyte, in front of whose anode, i.e. of the alcohol-consuming electrode, a membrane is arranged, which limits the transport of alcohol. The anode of this fuel cell has a catalyst for the electrochemical oxidation of the alcohol; the cathode has a catalyst for the electrochemical reduction of oxygen. The cathode is preferably developed to allow the conversion of atmospheric oxygen to permit operation of the measuring device with air.

The anode is a porous electrode in order to allow the carbon dioxide that forms during oxidation of the alcohol to escape.

The concentration of low-molecular alcohols is determined with the measuring device according to the invention. Alcohols of this type are, in particular, methanol ($CH_3OH$), ethanol ($C_2H_5OH$) and propanols ($C_3H_7OH$). This measuring device is preferably used for determining the concentration of methanol in the electrolyte of direct-methanol fuel cells. In addition, the measuring device has a compact type of construction, so that an additional moistening of the polymer electrolyte membrane is not necessary.

The anode consists advantageously of a porous supporting material, which is provided on both sides with a catalyst for the oxidation of alcohol. The supporting material, which serves as a gas offtake layer, is preferably a carbon paper or a fabric of carbon. The anode preferably contains a platinum/ruthenium catalyst (Pt/Ru); the cathode preferably contains a platinum catalyst (Pt). However, a platinum lattice can also be used, for example, as porous supporting material.

The diffusion-limiting membrane is advantageously a cation exchanger membrane, preferably a membrane having a poly(perfluoroalkylene)-sulfonic acid base; however, a membrane of polytetrafluoroethylene can also be used, for example. The ion-conducting membrane is advantageously an ion exchanger membrane, for example a membrane having a poly(perfluoroalkylene)-sulfonic acid base.

The invention shall be further explained using the following exemplary embodiment.

The applied measuring device has an anode in the form of a carbon paper, which is coated on both sides with a Pt/Ru catalyst; the catalyst coating amounts to about 10 $mg/cm^2$. The cathode consists of a carbon paper, which is provided with a Pt-catalyst (catalyst coating: about 4 $mg/cm_2$). The active cell surface amounts to 2 $cm^2$. A commercial ion exchanger membrane of Nafion having a thickness of about 120 μm is used as an ion-conducting membrane; a corresponding membrane having a thickness of about 170 μm is used as a diffusion-limiting membrane.

This measuring device is used for determining the concentration of methanol in the electrolyte of a direct-methanol fuel cell battery (DMFC=Direct Methanol Fuel Cell). For this purpose, the measuring device is installed in the fuel line, through which an aqueous methanol solution is conducted from a reservoir to the battery. The measuring device delivers a measuring signal that is dependent upon the methanol concentration. To this end, in the simplest case, the measuring device is loaded with a constant resistance and the cell voltage is used as a measuring signal. As a measuring signal, however, it is also possible to measure the cell current at a constant cell voltage.

The measuring device is loaded, for example, with a resistance of 1 Ω, and the voltage across this load is used as a measuring signal. The result ms an essentially linear dependency of the current drop (across the load) on the methanol concentration in the range of more or less up to 1 mole/l. The measuring range can be expanded by varying the thickness of the diffusion-limiting membrane. In addition, it turns out that the measuring device functions efficiently in response to changes in the methanol concentration.

What is claimed is:

1. A measuring device for determining the concentration of low-molecular alcohols in water or acids, consisting of:

a porous anode for electrochemical oxidation of alcohol a cathode for electrochemical reduction of oxygen an ion-conducting membrane arranged between the anode and cathode, and a diffusion-limiting membrane arranged on a side of the anode facing away from the ion-conducting membrane, wherein an aqueous electrolyte is not present between the anode and the cathode.

2. The measuring device according to claim 1, wherein the anode includes a porous supporting material having on both sides thereof a catalyst for the oxidation of alcohol.

3. The measuring device according to claim 2, wherein the anode contains a platinum/ruthenium catalyst.

4. The measuring device according to claim 3, wherein the cathode contains a platinum catalyst.

5. The measuring device according to claim 2, wherein the cathode contains a platinum catalyst.

6. The measuring device according to claim 5, wherein the diffusion-limiting membrane is a cation exchange membrane.

7. The measuring device according to claim 2, wherein the diffusion-limiting membrane is a cation exchange membrane.

8. The measuring device according to claim 7, wherein the cation exchange membrane is a membrane having a poly (perfluoroalkylene)-sulfonic acid base.

9. The measuring device according to claim 2, wherein the ion-conducting membrane is an ion exchange membrane.

10. The measuring device according to claim 1, wherein the anode contains a platinum/ruthenium catalyst.

11. The measuring device according to claim 10, wherein the cathode contains a platinum catalyst.

12. The measuring device according to claim 10, wherein the diffusion-limiting membrane is a cation exchange membrane.

13. The measuring device according to claim 1, wherein the cathode contains a platinum catalyst.

14. The measuring device according to claim 13, wherein the diffusion-limiting membrane is a cation exchange membrane.

15. The measuring device according to claim 14, wherein the cation exchange membrane is a membrane having a poly(perfluoroalkylene)-sulfonic acid base.

16. The measuring device according to claim 1, wherein the diffusion-limiting membrane is a cation exchange membrane.

17. The measuring device according to claim 16, wherein the cation exchange membrane is a membrane having a poly(perfluoroalkylene)-sulfonic acid base.

18. The measuring device according to claim 1, wherein the ion-conducting membrane is an ion exchange membrane.

* * * * *